(12) United States Patent
Kamiyama

(10) Patent No.: US 8,834,371 B2
(45) Date of Patent: Sep. 16, 2014

(54) ULTRASOUND DIAGNOSTIC APPARATUS AND ULTRASOUND IMAGE PROCESSING PROGRAM

(75) Inventor: Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 413 days.

(21) Appl. No.: 11/278,075

(22) Filed: Mar. 30, 2006

(65) Prior Publication Data

US 2006/0241431 A1 Oct. 26, 2006

(30) Foreign Application Priority Data

Mar. 31, 2005 (JP) .................................. 2005-104523

(51) Int. Cl.
| | |
|---|---|
| A61B 8/00 | (2006.01) |
| G06K 9/46 | (2006.01) |
| G01S 7/52 | (2006.01) |
| A61B 8/08 | (2006.01) |

(52) U.S. Cl.
CPC ........... *A61B 8/0825* (2013.01); *G01S 7/52074* (2013.01); *G01S 7/52077* (2013.01); *A61B 8/463* (2013.01); *G01S 7/52046* (2013.01)
USPC ............................ 600/443; 600/437; 382/190

(58) Field of Classification Search
USPC ............................ 600/437, 443; 382/260, 190
See application file for complete search history.

(56) References Cited

U.S. PATENT DOCUMENTS

| | | | | |
|---|---|---|---|---|
| 5,779,641 | A * | 7/1998 | Hatfield et al. | 600/443 |
| 5,954,653 | A | 9/1999 | Hatfield et al. | |
| 6,155,978 | A * | 12/2000 | Cline et al. | 600/443 |
| 6,360,027 | B1 * | 3/2002 | Hossack et al. | 382/294 |
| 6,421,454 | B1 * | 7/2002 | Burke et al. | 382/131 |
| 7,466,848 | B2 * | 12/2008 | Metaxas et al. | 382/128 |
| 2003/0097068 | A1 | 5/2003 | Hossack et al. | |
| 2005/0053305 | A1 * | 3/2005 | Li et al. | 382/260 |
| 2006/0030768 | A1 * | 2/2006 | Ramamurthy et al. | 600/407 |

FOREIGN PATENT DOCUMENTS

| | | |
|---|---|---|
| EP | 1 411 370 A1 | 4/2004 |
| JP | 61-189476 | 8/1986 |
| JP | 64-5534 | 1/1989 |
| JP | 4-28354 | 1/1992 |
| JP | 7-116161 | 5/1995 |
| JP | 11-28211 | 2/1999 |
| JP | 2000-238 | 1/2000 |
| JP | 2001-238884 | 9/2001 |

(Continued)

OTHER PUBLICATIONS

English translation of JP 2003-61964 as provided by the IPDL tool.*

(Continued)

*Primary Examiner* — Katherine Fernandez
(74) *Attorney, Agent, or Firm* — Oblon, Spivak, McClelland, Maier & Neustadt, L.L.P.

(57) ABSTRACT

In ultrasound diagnosis of, for example, the breasts, a microstructure extraction image in which a microstructure is actively extracted is generated by performing MIP processing together with CFAR processing of removing speckle patterns from a B mode image (tissue image). The generated microstructure extraction image is displayed in the dual display form or the triplex display form, together with, for example, a B mode image before CFAR processing or a B mode image after CFAR processing.

20 Claims, 14 Drawing Sheets

(56) References Cited

FOREIGN PATENT DOCUMENTS

| | | |
|---|---|---|
| JP | 2003-61964 | 3/2003 |
| JP | 3413905 | 4/2003 |
| JP | 3596792 | 9/2004 |
| JP | 2004-321582 | 11/2004 |

OTHER PUBLICATIONS

Yamaguchi et al., "Extraction of Quantitative Three-Dimensional Information from Ultrasonic Volumetric Images of Cirrhotic Liver", Jpn. J. Appl. Phys., vol. 39, May 2000; pp. 3266-3269.*

U.S. Appl. No. 11/928,803, filed Oct. 30, 2007, Yoshida, et al.

Thomas R. Nelson, et al., "Three-Dimensional Ultrasound Imaging", Ultrasound in Medicine and Biology, XP004295279, vol. 24, No. 9, Dec. 1998, pp. 1243-1270.

Tadashi Yamaguchi, et al., "Examination of the Spatial Correlation of Statistics Information in the Ultrasonic Echo from Diseased Liver", Jpn. J. Appl. Phys., XP-002414306, vol. 41, No. 5B, May 2002, pp. 3585-3589.

Tadashi Yamaguchi, et al., "Estimation of the Scatterer Distribution of the Cirrhotic Liver using Ultrasonic Image", Jpn. J. Appl. Phys., XP-002414307, vol. 37, No. 5B, May 1998, pp. 3093-3096.

Yongjian Yu, et al., "Detection of Radioactive Seeds in Ultrasound Images of the Prostate", IEEE, XP-010563762, vol. 1 of 3. Cone. 8, Oct. 7, 2001, pp. 319-322.

D. Herrington, et al., "Image Processing and Display of 3D Intra-Coronary Ultrasound Images", IEEE, XP-010026714, vol. Meeting 18, Sep. 23, 1991, pp. 349-352.

Petri M. Tuomola, et al., "Body-Centered Visualisation for Freehand 3-D Ultrasound", Ultrasound in Medicine and Biology, XP-004295595, vol. 26, No. 4, May 2000, pp. 539-550.

U.S. Appl. No. 12/484,465, filed Jun. 15, 2009, Okamura, et al.

Office Action issued May 24, 2011, in Japanese Patent Application No. 2006-091059 (with English-Language translation).

* cited by examiner

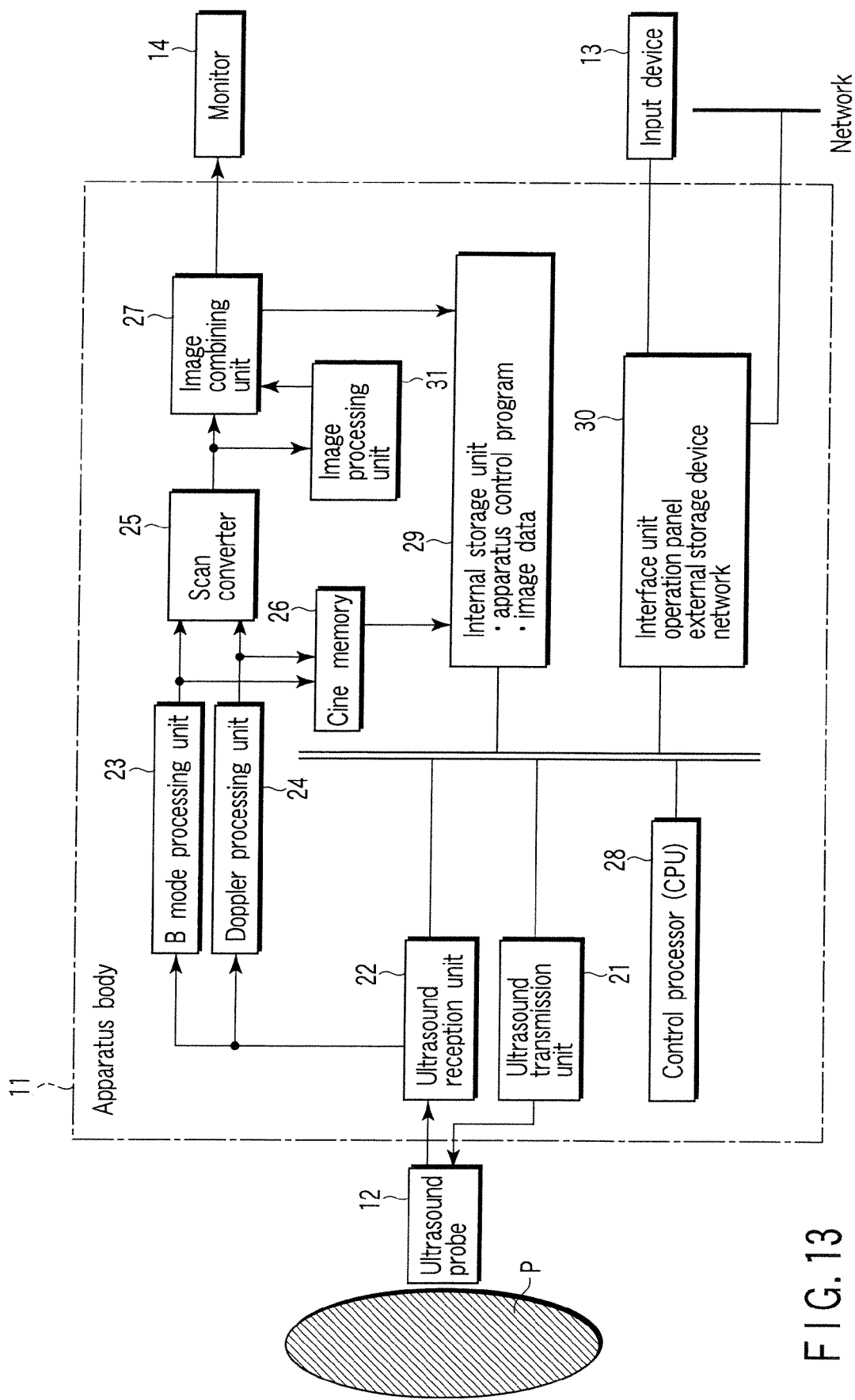
F I G. 13

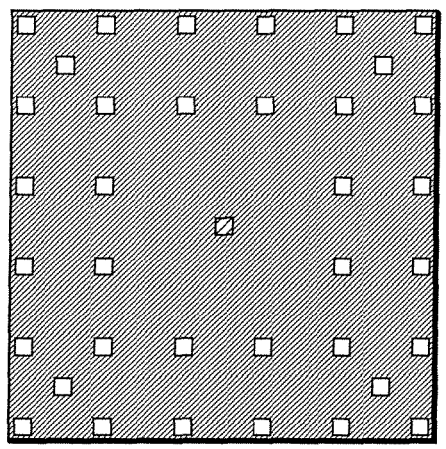
F I G. 15A
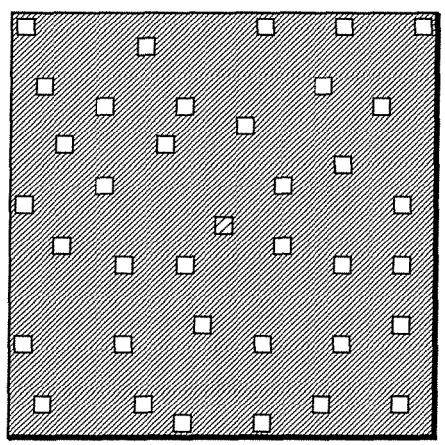
F I G. 15B
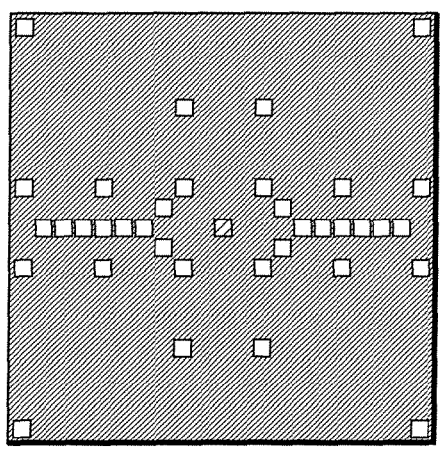
F I G. 15C

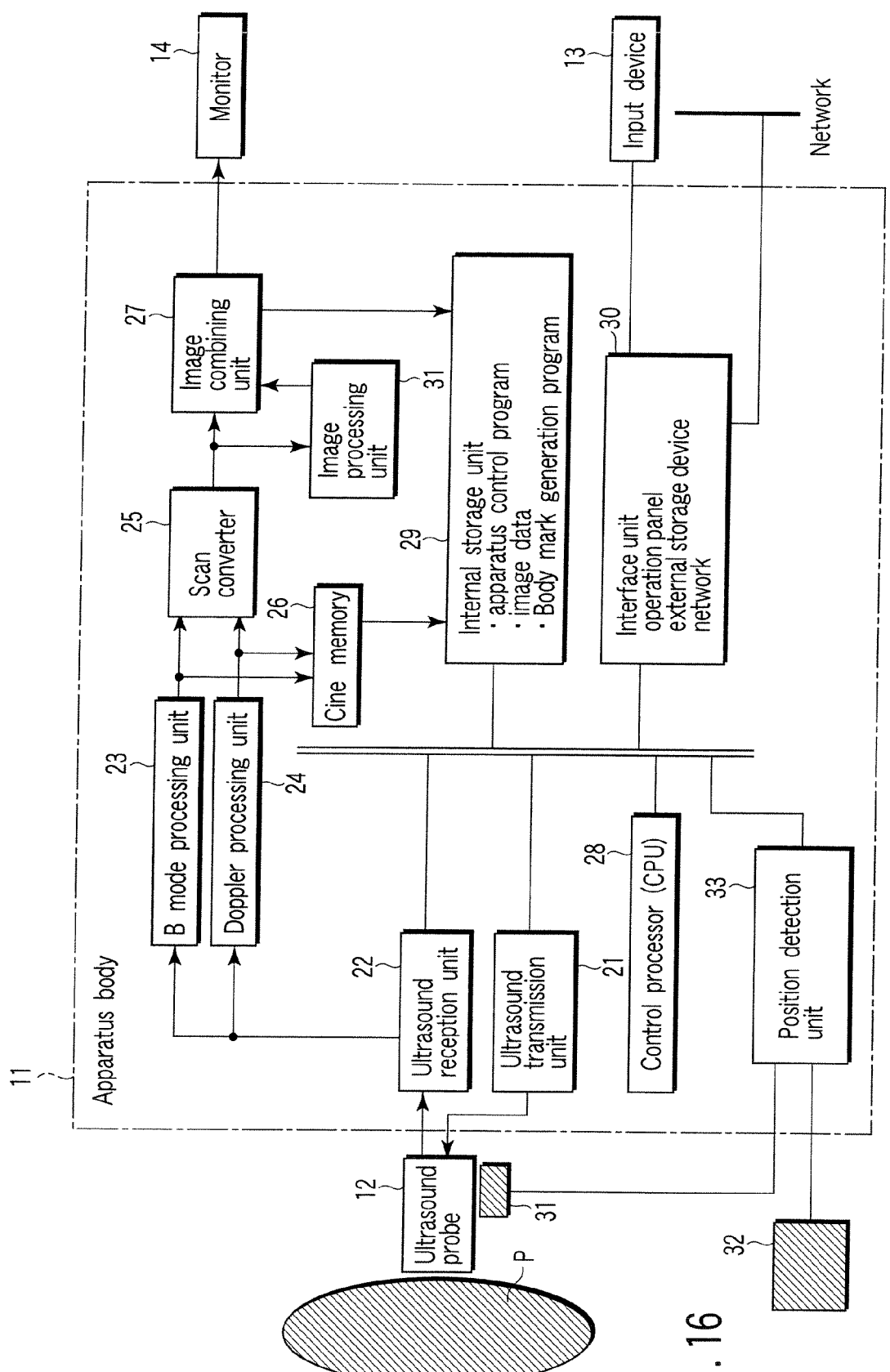
F I G. 16

ULTRASOUND DIAGNOSTIC APPARATUS AND ULTRASOUND IMAGE PROCESSING PROGRAM

CROSS-REFERENCE TO RELATED APPLICATIONS

This application is based upon and claims the benefit of priority from prior Japanese Patent Application No. 2005-104523, filed Mar. 31, 2005, the entire contents of which are incorporated herein by reference.

BACKGROUND OF THE INVENTION

1. Field of the Invention

The present invention relates to an ultrasound diagnostic apparatus and ultrasound image processing program which actively extract and display microstructures in living organs and the like from echo signals from tissue.

2. Description of the Related Art

Ultrasound diagnosis makes it possible to display how the heart beats or the embryo moves in real time by simple operation of tapping an ultrasound probe on the body surface, and allows repetitive examination because it is highly safe. In addition, the system size is smaller than other diagnostic equipment such as X-ray, CT, and MRI equipment, and hence the apparatus can be moved to a bed side to allow easy examination. Ultrasound diagnostic apparatuses vary depending on the types of functions which they have. For example, an ultrasound diagnostic apparatus having a size that allows an operator to carry it with his/her one hand has been developed, and ultrasound diagnosis is free from the influence of radiation exposure such as X-ray exposure. Therefore, this apparatus can be used in obstetrical treatment, treatment at home, and the like.

Such types of ultrasound diagnosis include breast cancer early diagnosis. It is known that in many cases, micro calcification occurs in breast tissue as a symptom of breast cancer. One or a few calcified lesions are scattered in local portions. Lime is harder than living tissue, and hence reflects well ultrasound waves. Therefore, such a calcified lesion is expected to exhibit high brightness on an image. It is, however, difficult to extract such a lesion in an image by visual recognition even if it has a size of about several hundred μm.

In some cases, interference fringes called speckle patterns due to random interference between ultrasound waves are produced on an ultrasound image. On the other hand, this pattern is very similar to a microstructure such as a micro calcified substance which tends to be overlooked in, for example, the above breast cancer diagnosis, and hence sometimes becomes misleading image information. For this reason, in the above breast cancer diagnosis or the like which requires no speckle pattern, in order to remove the pattern, for example, the following processing is performed: spatial compounding (see, for example, patent references 1, 2, 3, and 4), CFAR (Contrast False Alarm Rate) processing, similarity filter processing and other speckle reduction processes, MIP (Maximum Intensity Projection) processing, and image condition adjustment. Note that these techniques are disclosed in, for example, Jpn. Pat. Appln. KOKAI Publication Nos. 61-189476, 2001-238884, 2003-61964, and 2004-321582. Although not included in the ultrasound field, various attempts to automatically recognize micro calcification have been reported mainly as applications of X-ray diagnostic images, as disclosed in, for example, U.S. Pat. No. 3,596,792.

However, for example, the following problems arise in the above conventional techniques for properly observing microstructures by removing speckle patterns.

In speckle reduction using CFAR processing, although the contrast ratio of a microstructure can be relatively increased, in a case wherein a living body is three-dimensionally scanned to search for a minute substance, oversight still occurs. Even if, for example, a microstructure is displayed in a given frame, the time required to move a scan slice is generally shorter than the time required to find (acknowledge) the microstructure.

MIP processing is suitable for the observation of an approximate shape of an organ. If, however, a speckle pattern and a microstructure are superimposed on each other, the contrast ratio of a minute substance decreases. Therefore, an image having undergone MIP processing alone is not sufficient for the observation of a microstructure.

In addition, in image quality condition adjustment, e.g. dynamic range or gain, if the operator manually makes adjustments, an image which is suitable to some extent can be obtained. If, however, the operator makes wrong settings, a microstructure may not be displayed or speckles may remain. In addition, since optimal set values vary depending on the state of a subject (attenuation due to subcutaneous fat), it is no use to record optimal values. Furthermore, the image based on the above set values does not often allow the operator to see an approximate shape of an organ in the prior art. With this image alone, therefore, it may sometimes become difficult to specify a slice.

BRIEF SUMMARY OF THE INVENTION

The present invention has been made in consideration of the above situation, and has as its object to provide an ultrasound diagnostic apparatus and ultrasound image processing program which allow to properly observe microstructures such as micro calcified substances which tend to be overlooked in, for example, breast cancer examination.

According to an aspect of the present invention, there is provided that an ultrasound diagnostic apparatus which acquires an ultrasound image by ultrasound-scanning a subject, and comprises: an ultrasound transmission/reception unit which transmits ultrasound waves to the subject, receives the ultrasound waves from the subject and generates echo signals of a plurality of frames on the basis of the received ultrasound waves; an image generating unit which generates a first image of the plurality of frames by performing signal processing of reducing a speckle pattern component included in each of the echo signals of the plurality of frames, and generates a second image by performing maximum value projection processing or maximum value holding processing using the first image of the plurality of frames; and a display unit which displays the generated second image.

According to another aspect of the present invention, there is provided that an ultrasound diagnostic apparatus which acquires an ultrasound image by ultrasound-scanning a subject, and comprises: an ultrasound transmission/reception unit which transmits ultrasound waves to the subject, receives the ultrasound waves from the subject and generates echo signals of a plurality of frames on the basis of the received ultrasound waves; an image generating unit which generates a first image of the plurality of frames by performing maximum value projection processing or maximum value holding processing using the echo signals of the plurality of frames and generates a second image by performing signal processing of reducing a speckle pattern component included in the first image; and a display unit which displays the generated second image.

According to yet another aspect of the present invention, there is provided that a computer program product configured to store program instruction for execution on a computer system enabling the computer system to perform: generating a first image of a plurality of frames by performing signal processing of reducing a speckle pattern component included in echo signals of a plurality of frames acquired by an ultrasound diagnostic apparatus; generating a second image by performing maximum value projection processing or maximum value holding processing using the first image of the plurality of frames; and displaying the generated second image.

According to yet another aspect of the present invention, there is provided that a computer program product configured to store program instruction for execution on a computer system enabling the computer system to perform: generating a first image of the plurality of frames by performing maximum value projection processing or maximum value holding processing using echo signals of a plurality of frames acquired by an ultrasound diagnostic apparatus; generates a second image by performing signal processing of reducing a speckle pattern component included in the first image; and displaying the generated second image.

According to yet another aspect of the present invention, there is provided that a control method of an ultrasound diagnostic apparatus which acquires an ultrasound image by ultrasound-scanning a subject, which comprises: transmitting ultrasound waves to the subject; receiving the ultrasound waves from the subject; generating echo signals of a plurality of frames on the basis of the received ultrasound waves; generating a first image of the plurality of frames by performing signal processing of reducing a speckle pattern component included in each of the echo signals of the plurality of frames; generating a second image by performing maximum value projection processing or maximum value holding processing using the first image of the plurality of frames; and a display unit which displays the generated second image.

According to yet another aspect of the present invention, there is provided that a control method of an ultrasound diagnostic apparatus which acquires an ultrasound image by ultrasound-scanning a subject, which comprises: transmitting ultrasound waves to the subject; receiving the ultrasound waves from the subject; generating echo signals of a plurality of frames on the basis of the received ultrasound waves; generating a first image of the plurality of frames by performing maximum value projection processing or maximum value holding processing using the echo signals of the plurality of frames; generating a second image by performing signal processing of reducing a speckle pattern component included in the first image; and a display unit which displays the generated second image.

BRIEF DESCRIPTION OF THE SEVERAL VIEWS OF THE DRAWING

FIG. 13 is a block diagram showing the arrangement of an ultrasound diagnostic apparatus 1 according to the third embodiment;

FIGS. 15A, 15B, and 15C are views each showing an example of a kernel used in CFAR processing executed by an ultrasound diagnostic apparatus according to the fifth embodiment;

FIG. 16 is a block diagram showing an arrangement obtained by making the ultrasound diagnostic apparatus 1 according to the sixth embodiment have a scanning range determination function;

DETAILED DESCRIPTION OF THE INVENTION

Figure 1:
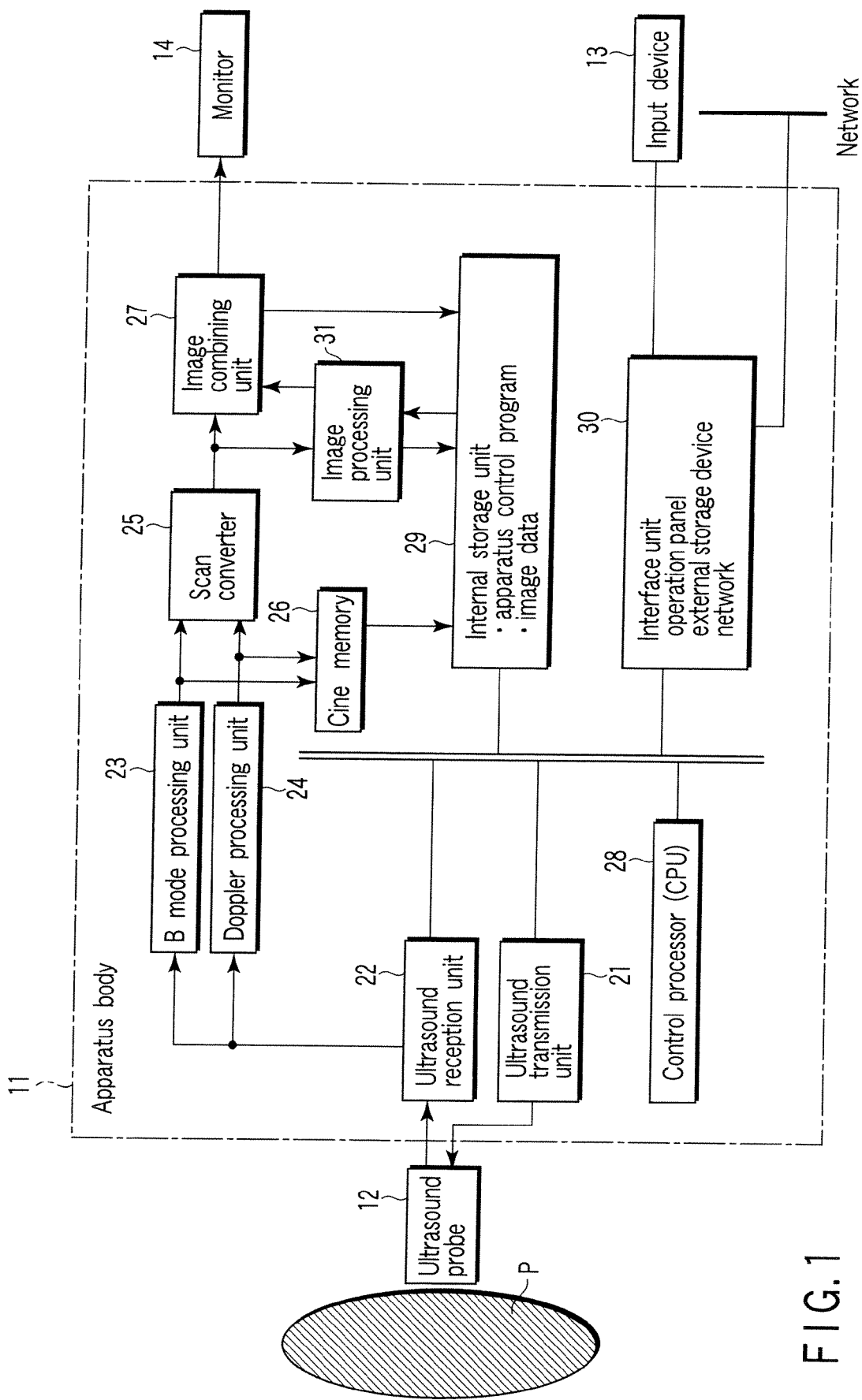
FIG. 1 is a block diagram showing the arrangement of an ultrasound diagnostic apparatus 1 according to the first embodiment.

The first to sixth embodiments of the present invention will be described with reference to the views of the accompanying drawing. Note that the same reference numerals in the following description denote constituent elements having substantially the same functions and arrangements, and a repetitive description will be made only when required. For a concrete description of each embodiment, assume that a diagnosis target is a breast. However, a technique according to the present invention is not limited to this and is also effective for other predetermined organs such as the liver and the pancreas as well as the breasts.

First Embodiment

FIG. 1 is a block diagram of an ultrasound diagnostic apparatus 1 according to this embodiment. As shown in FIG. 1, the ultrasound diagnostic apparatus 1 comprises an ultrasound probe 12, input device 13, monitor 14, ultrasound transmission unit 21, ultrasound reception unit 22, B mode processing unit 23, Doppler processing unit 24, scan converter 25, cine memory 26, image combining unit 27, control processor (CPU) 28, internal storage unit 29, interface unit 30, and image processing unit 31. The function of each constituent element will be described below.

The ultrasound probe 12 generates ultrasound waves on the basis of a driving signal from the ultrasound transmission unit 21, and includes a plurality of piezoelectric vibrators for converting reflected waves from a subject into electrical signals, an aligning layer provided for the piezoelectric vibrators, a backing material for preventing the backward propagation of ultrasound waves from the piezoelectric vibrators. When ultrasound waves are transmitted from the ultrasound probe 12 to a subject P, the ultrasound waves are sequentially reflected by an acoustic-impedance discontinuous surface in tissue in the body and received as an echo signal by the ultrasound probe 12. The amplitude of this echo signal depends on the differences between the acoustic impedances on the discontinuous surface by which the ultrasound waves are reflected. Echoes generated when transmitted ultrasound pulses are reflected by a moving blood flow, a moving cardiac wall, or the like are subjected to frequency shift depending on the velocity component of the moving object in the ultrasound transmission direction owing to the Doppler effect.

The input device 13 is connected to an apparatus body 11 and has various kinds of switches, buttons, a trackball 13s, a mouse 13c, a keyboard 13d, and the like which are used to input, to the apparatus body 11, various kinds of instructions and conditions, an instruction to set a region of interest (ROI), various kinds of image quality condition setting instructions, and the like from an operator. When, for example, the operator operates the end button or FREEZE button of the input device 13, the transmission/reception of ultrasound waves is terminated, and the ultrasound diagnostic apparatus is set in a temporary stop state.

The monitor 14 displays morphological information or blood flow information in the living body as an image on the basis of a video signal from the scan converter 25.

The ultrasound transmission unit 21 has a trigger generating circuit, delay circuit, pulser circuit, and the like (none are shown). The pulser circuit repeatedly generates rate pulses for the formation of transmission ultrasound waves at a predetermined rate frequency fr Hz (period: 1/fr sec). The delay circuit gives each rate pulse the delay time required to focus an ultrasound wave into a beam for each channel and determine a transmission directivity. The trigger generating circuit applies a driving pulse to the probe 12 at the timing based on this rate pulse.

Note that the ultrasound transmission unit 21 has a function of instantly changing a transmission frequency, a transmission driving voltage, and the like to execute a predetermined scan sequence on the basis of an instruction from the control processor 28. The transmission driving voltage changing operation, in particular, is realized by a linear amplifier type oscillation circuit capable of instantly switching the value of a transmission driving voltage or a mechanism of electrically switching a plurality of power supply units.

The ultrasound reception unit 22 has an amplifier circuit, A/D converter, adder, and the like (none are shown). The amplifier circuit amplifies echo signals received through the ultrasound probe 12 on a channel basis. The A/D converter gives each amplified echo signal the delay time required to determine a reception directivity. The adder then performs addition processing. With this addition, the reflection component of the echo signal from the direction corresponding to the reception directivity is enhanced, and a synthetic beam for ultrasound transmission/reception is formed in accordance with the reception directivity and transmission directivity.

The B mode processing unit 23 receives the echo signal from the ultrasound transmission unit 21, and performs logarithmic amplification, envelope detection processing, and the like, thereby generating data whose signal strength is represented by a brightness level. This data is transmitted to the scan converter 25 and is displayed as a B mode image representing the strength of a reflected wave as a brightness on the monitor 14.

The Doppler processing unit 24 frequency-analyzes velocity information from the echo signal received from the ultrasound transmission unit 21 to extract a blood flow, tissue, and contrast medium echo component by the Doppler effect, and obtains blood flow information such as an average velocity, variance, and power. The obtained blood flow information is sent to the scan converter 25, and is color-displayed as an average velocity image, variance image, power image, and a combination image thereof on the monitor 14.

The scan converter 25 converts the scanning line signal sequence obtained by ultrasound scanning into a scanning line signal sequence in a general video format typified by that used for TVs and the like, and generates an ultrasound diagnostic image as a display image. The scan converter 25 is equipped with a storage memory which stores image data. For example, after diagnosis, the operator can call up images recorded during examination. Note that data before it is input to the scan converter 25 is sometimes called "raw data".

The cine memory 26 is a memory which stores, for example, ultrasound images corresponding to a plurality of frames immediately before freezing. An ultrasound moving image can also be displayed by continuously displaying (cine-displaying) the images stored in the cine memory 26.

The image combining unit 27 combines an image received from the scan converter 25 or the image processing unit 31 with the character information of various kinds of parameters, scale marks, and the like, and outputs the resultant data as a video signal to the monitor 14. The image combining unit 27, in particular, generates a composite image by combining a B mode image before speckle reduction which is received from the scan converter 25, a B mode image before speckle reduction which is received from the image processing unit 31, and an image after MIP processing.

The control processor 28 is a control unit which has a function as an information processing apparatus (computer) and controls the operation of this ultrasound diagnostic apparatus body. The control processor 28 reads out control programs for executing image generation/display and the like from the internal storage unit 29, maps them in its internal memory, and executes computation/control and the like associated with various kinds of processing.

The internal storage unit 29 stores a scan sequence (to be described later), a control program for executing image generation/display processing, diagnosis information (a patient ID, findings by a doctor, and the like), a diagnosis protocol, transmission/reception conditions, a CFAR processing control program, body mark generation program, and other data. The internal storage unit 29 is also used to, for example, store images in the cine memory 26, as needed. Data from the internal storage unit 29 can be transferred to an external peripheral apparatus through the interface unit 30.

The interface unit 30 is an interface associated with the input device 13, a network, and a new external storage device (not shown). The interface unit 30 can transfer data such as ultrasound images, analysis results, and the like which are obtained by this apparatus to other apparatuses through a network.

The image processing unit 31 executes various kinds of image processing such as speckle reduction processing such as CFAR processing and MIP processing using a plurality of frame images with respect to B mode images and the like received from the scan converter 25 or the internal storage unit 29 under the control of the control processor 28.

(Microstructure Extraction Function)

The microstructure extraction function of the ultrasound diagnostic apparatus 1 will be described next. This function generates an image with microstructures being actively extracted (microstructure extraction image) by removing speckle patterns from a B mode image (tissue image) while performing MIP processing in diagnosis of the breasts, liver, pancreas, and the like.

In this embodiment, for clarification, CFAR processing is employed as a technique for removing speckle patterns from B mode images. However, the present invention is not limited to this and may use various other kinds of methods, e.g., a spatial compounding method of reducing display brightness after smoothing speckle patterns by superimposing transmission/reception signals in different directions, and a similarity filter method of removing speckle patterns by using statistical characteristics. Some conventional spatial compounding methods use a display form in which speckles are only smoothed and the overall brightness is kept unchanged. From the viewpoint of the gist of this embodiment, however, spatial compounding is preferably performed such that the brightness of speckle portions is reduced while speckles are smoothed.

The term "CFAR processing" is used in the radar field, and in the description of this embodiment the word "CFAR" is used for the sake of convenience to more concretely explain the term in association with the field. However, this processing is not limited to a method used in the radar field or a method using statistics values in the strict sense.

Figure 2A:
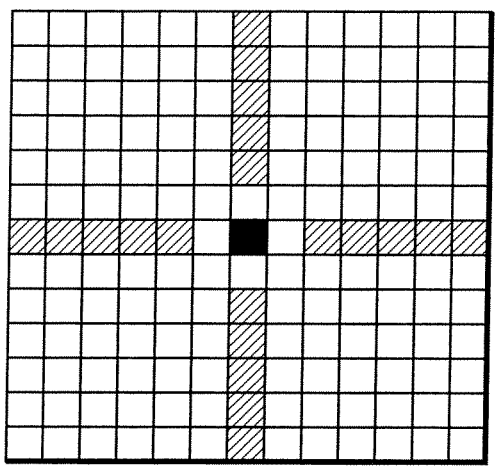
FIGS. 2A and 2B are views for explaining the concept of CFAR processing.
Figure 2B:
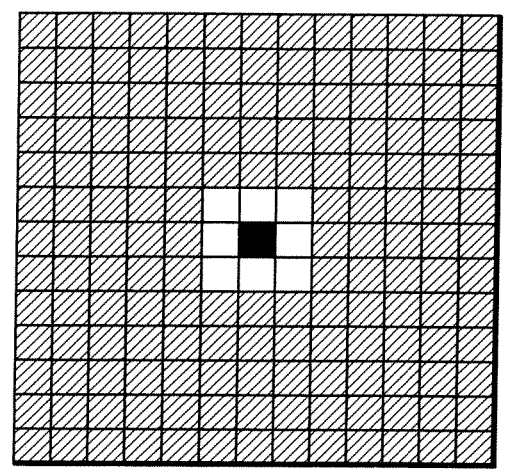
Figure 3:
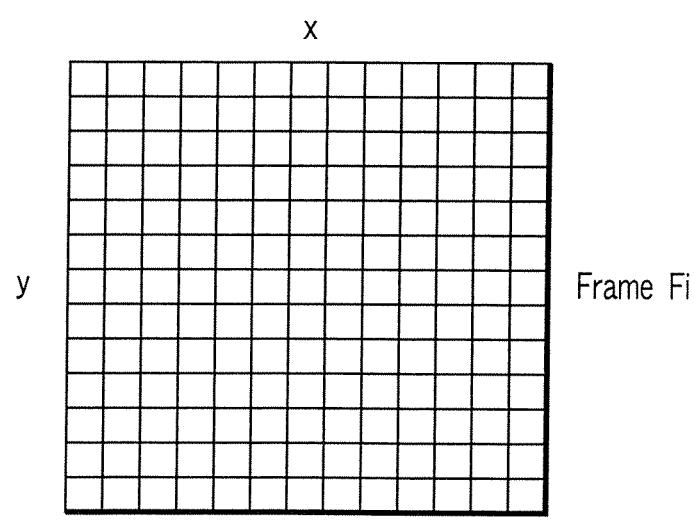
FIG. 3 is a view for explaining the concept of CFAR processing.

FIGS. 2A to 3 are views for explaining the concept of CFAR processing. Referring to FIG. 2A, the white rectangles represent general pixels constituting an ultrasound image, the black rectangle represents a target pixel $P_i$ of the pixels constituting the ultrasound image, and the intermediate color (between white and black) rectangles represent pixels (neighboring pixels) which are located adjacent to the target pixel $P_i$ and used for averaging processing in (1) to be described later.

CFAR processing is performed by, for example, procedures (1) to (3) below.

(1) First of all, the average brightness value of the neighboring pixels of the target pixel $P_i$ is obtained for each target pixel $P_i$. In this case, the target pixel $P_i$ may be excluded from the average brightness calculation of the neighboring pixels to prevent the brightness of the target pixel itself from influencing the average value.

(2) The value obtained by subtracting the obtained average value from the pixel value of the target pixel $P_i$ is defined as a computation result $K_i$ corresponding to the position of the target pixel $P_i$ and stored in the internal storage unit 29. This computation processing is executed for all the target pixels $P_i$.

(3) Subsequently, if $K_i \geq T$ where T is a predetermined threshold, the target pixel $P_i$ is displayed (extraction of a microstructure) using the original brightness. If $K_i < T$, the brightness value of the target pixel $P_i$ is set to 0 so as not to display the pixel (so as to remove it). These processes are executed for all target pixels $P_i$ to execute CFAR processing associated with this image.

In determination in procedure (3) described above, if $K_i \geq T$, the brightness may be set to $K_i$ to display the target pixel $P_i$, whereas if $K_i < T$, the brightness value of the target pixel $P_i$ may be set to 0 so as not to display the pixel.

In the case shown in FIG. 2A, neighboring pixels are provided in a cruciform shape to shorten the computation processing time. However, the arrangement of neighboring pixels is not limited to this. If, for example, no problem arises in terms of the time required for computation processing, the average value of neighboring pixels arranged in a wide range may be obtained, as shown in FIG. 2B.

This CFAR processing is effective in extracting a signal having a luminance deviating from speckle variations. As a computation technique having a similar effect, high-pass filter processing (signal processing of extracting only high-frequency components) is available. Although an arrangement using a high-pass filter instead of this CFAR processing may be used, CFAR processing is superior in some cases in speckle pattern reduction.

MIP processing will be described next. Let $K_i(x, y)$ be the brightness value at a position (x, y) in a frame $F_i$ (i=1, 2, 3, ..., N). Computing an MIP image with respect to N frames $F_1, F_2, ..., F_N$ is equivalent to obtaining the maximum value of the brightnesses of all the frames for all the coordinates (x, y). This can be expressed as follows:

$$M_i(x,y)=\max[K_i(x,y), (i=1,2,3,...,N)]$$

where max [ ] indicates computation for the selection of the maximum value within [ ]. An MIP image is a new image frame generated by using the computation result $M_i(x, y)$.

The above computation has exemplified the MIP processing performed after all the N image frames are acquired. In contrast to this, even if all N target frames are not acquired, MIP processing can be performed by comparing the pixel values of corresponding pixels of newly acquired one image and of one image acquired immediately preceding it and always tracing a larger pixel value (peak trace processing or maximum value holding computation). More specifically, a brightness $K_1$ of the first frame is input to $M_1$ first. A brightness value $K_2$ of the second frame is then compared with $M_1$, and a higher value is assigned to $M_2$. When this processing is repeated, $M_N$ at the Nth operation becomes the MIP of all the N frames. The above processing can be described as follows:

$$M_1 = K_i(x,y)$$

$$M_i(x,y)=\max[K_i(x,y),M_i(x,y)]$$

for (i=1, 2, 3, ..., N)

A microstructure extraction image generated by performing the above CFAR processing and MIP processing for a B mode image (tissue image) will be described next.

Figure 4A:
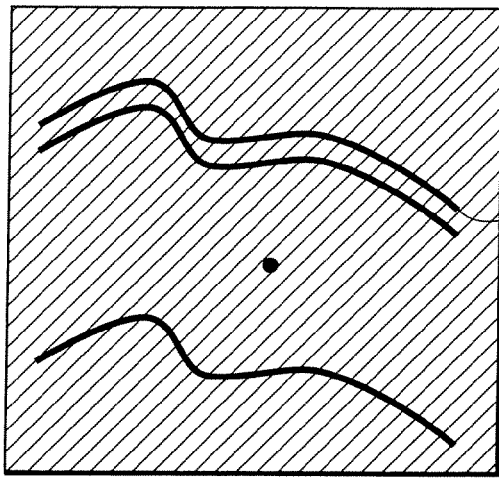
FIG. 4A is a view schematically showing a general B mode image.
Figure 4B:
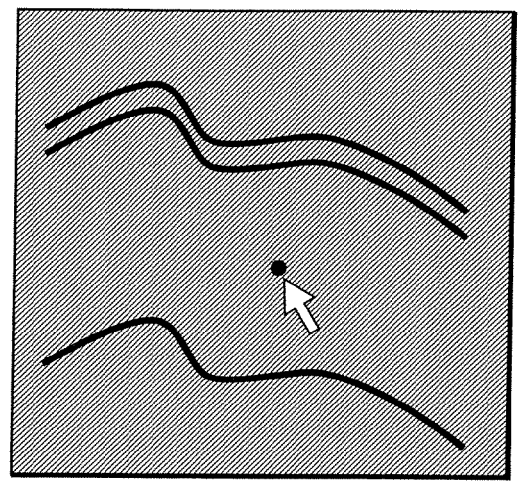
FIG. 4B is a view schematically showing an image obtained by performing CFAR processing for a B mode image.
Figure 4C:
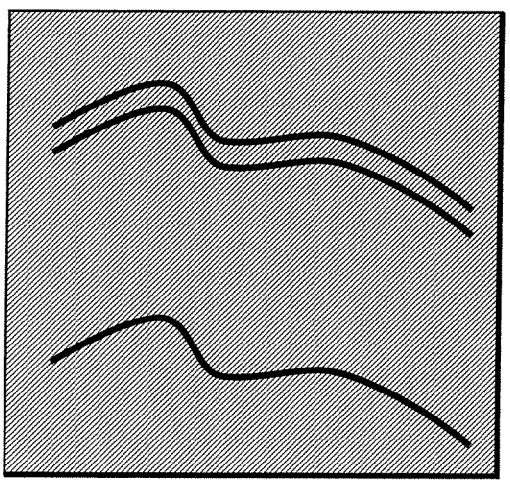
FIG. 4C is a view schematically showing an image obtained by performing MIP processing for a B mode image.
Figure 4D:
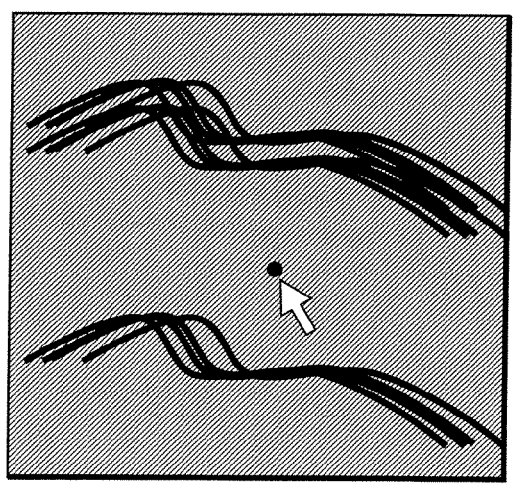
FIG. 4D is a view schematically showing a microstructure extraction image generated by performing CFAR processing and MIP processing for a B mode image.
Figure 4E:
FIG. 4E is a picture showing a general B mode image.
Figure 4F:
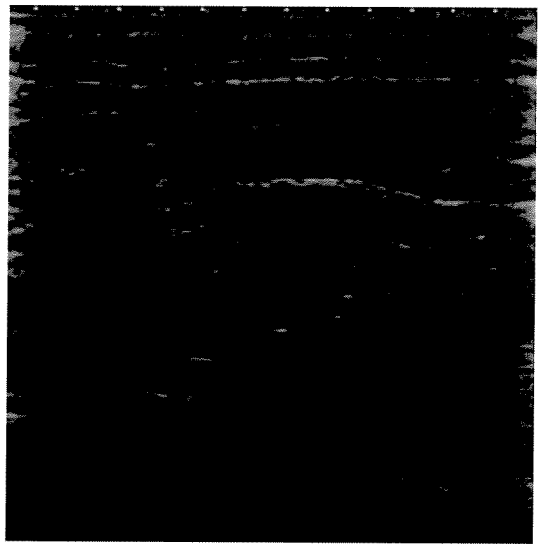
FIGS. 4F and 4G are pictures showing an image obtained by performing CFAR processing for the B mode image.
Figure 4G:
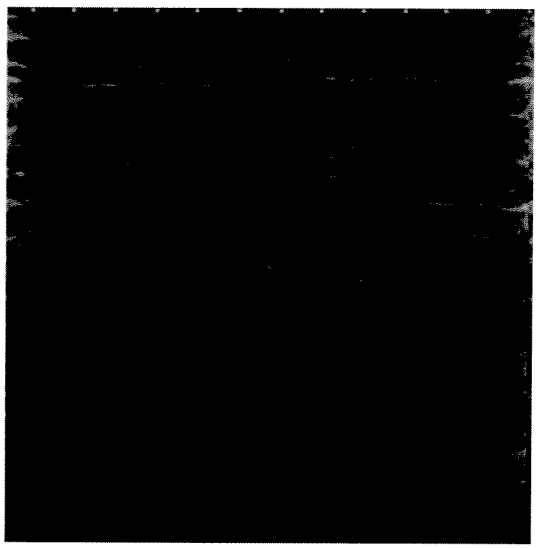
Figure 4H:
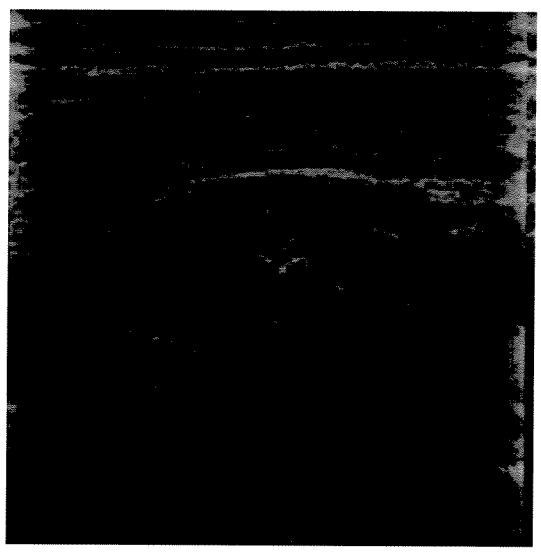
FIG. 4H is a picture showing a microstructure extraction image generated by performing CFAR processing and MIP processing for the B mode image.

FIG. 4A is a view schematically showing a general B mode image. FIGS. 4B and 4C are views each schematically showing an image obtained by performing CFAR processing for the B mode image. FIG. 4D is a view schematically showing a microstructure extraction image generated by performing CFAR processing and MIP processing for the B mode image. FIG. 4E is a picture showing a general B mode image. FIGS. 4F and 4G are pictures showing an image obtained by performing CFAR processing for the B mode image. FIG. 4H is a picture showing a microstructure extraction image generated by performing CFAR processing and MIP processing for the B mode image.

As shown in FIGS. 4A and 4E, the B mode image obtained by scanning an actual living body is displayed with a speckle pattern SP being superimposed thereon. It is difficult to instantly recognize the microstructure on the image. According to the image shown in FIGS. 4B and 4F to which CFAR processing has been performed, the speckle pattern SP shown in FIGS. 4A and 4E is removed, and only the microstructure (indicated by the arrow in FIG. 4B) and tissue boundary are left, thereby improving the visibility. In practice, however, since the living body is three-dimensionally scanned, the image shown in FIGS. 4B and 4F is obtained for a moment. Therefore, the microstructure on the image shown in FIGS. 4B and 4F disappears from the image as shown in FIGS. 4C and 4G, and cannot be displayed for a time sufficient for diagnosis.

In contrast, according to a microstructure extraction image, if any one of images from which the speckle pattern has been removed by CFAR processing captures the microstructure, the microstructure is always reflected in the microstructure extraction image by MIP processing, as shown in FIG. 4D. In addition, the microstructure extraction image can be displayed as a still image for a time sufficient for diagnosis.

In addition, according to this microstructure extraction function, a frame of the B mode image in which the microstructure on the microstructure extraction image is acquired can be specified.

Figure 5:
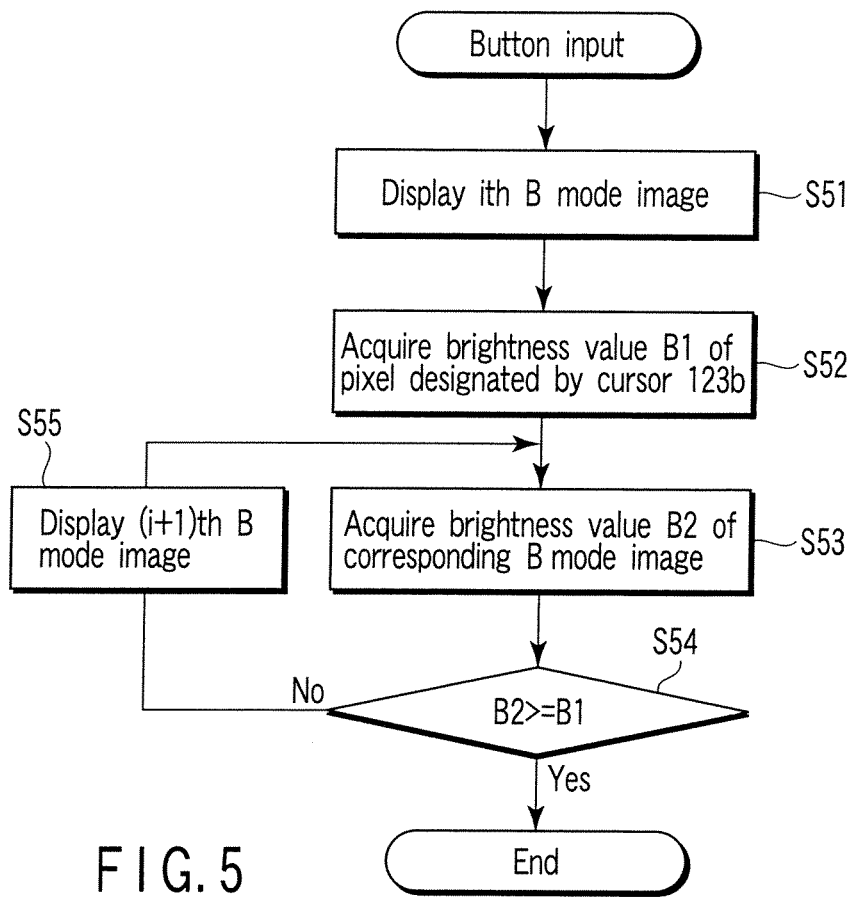
FIG. 5 is a flowchart showing the flow of processing of specifying a frame of the above B mode image.
Figure 6:
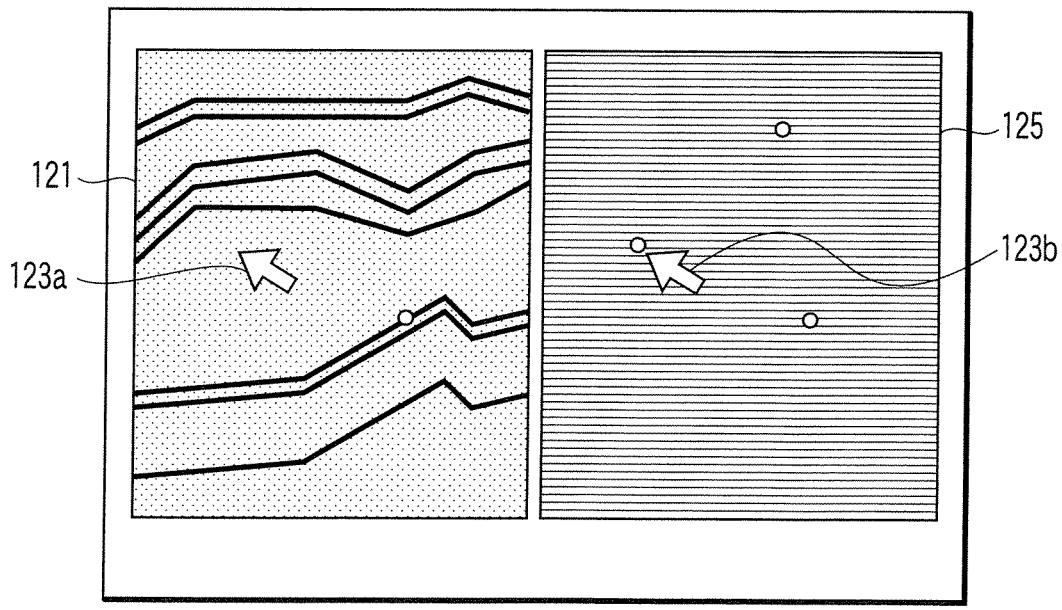
FIG. 6 is a view showing one ultrasound image display form obtained by the ultrasound diagnostic apparatus 1.

FIG. 5 is a flowchart showing the flow of processing of specifying the above B mode image frame. FIG. 6 shows an example of a display form (Dual display) used in this B mode image frame specifying processing. As shown in FIGS. 5 and 6, assume that a microstructure extraction image 125 comprises the ith to (i+N)th B mode images.

First of all, the ith B mode image is displayed (step S51), a brightness value $B_1$ at the position indicated by a cursor 123B on the MIP image is acquired (step S52).

After a brightness value $B_2$ at a position spatially corresponding to the position indicated by the cursor 123B is acquired on the ith B mode image (step S53), $B_1$ and $B_2$ are compared (step S54). If $B_2 < B_1$ is determined upon this comparison, it is determined that the B mode image is not a desired image, and the next (i+1)th B mode image is displayed (step S55). The processing in step S53 is then repeatedly executed. If it is determined upon comparison in step 54 that $B_2 \geq B_1$, it is determined that this image is a B mode image. The algorithm is then terminated.

In this case, a B mode image is sequentially displayed in accordance with specifying processing. However, the display of this image may be omitted until the end of the search, and only the B mode image as a specifying result may be finally displayed.

The image generated by this microstructure extraction function is displayed on a window of the monitor 14 in a predetermined form such as the single display form of singly displaying the image on the monitor 14, the Dual display form, or the Triplex display form.

In this case, the single display form is used to singly display the image on the window of the monitor 14.

Figure 7:
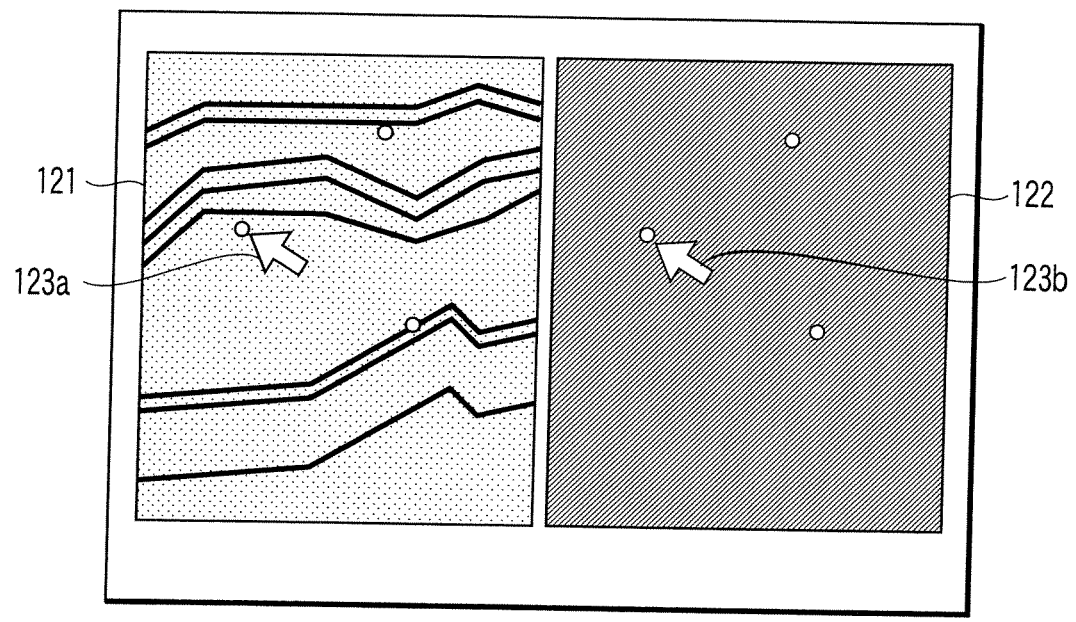
FIG. 7 is view showing another ultrasound image display form obtained by the ultrasound diagnostic apparatus 1.

In the dual display form, the window on the monitor 14 is divided into two parts to simultaneously display different kinds of images. In general, a still image taken in the past is displayed on one part, and a live image currently obtained by scanning is displayed on the other part. However, there is available a conventional technique of displaying live images on the two parts, e.g., displaying a B mode live image on one part and a Doppler image on the other part. In this embodiment, using this Dual display form makes it possible to display an arbitrary combination of a B mode image before CFAR processing, a B mode image after CFAR processing, and a microstructure extraction image. For example, as shown in FIG. 6, the microstructure extraction image 125 and a B mode image 121 in which a microstructure 123b (123a) on the microstructure extraction image is acquired can be simultaneously displayed. In addition, before the generation of a microstructure extraction image, a B mode image 121 before CFAR processing and a B mode image 122 after CFAR processing can be simultaneously displayed, as shown in FIG. 7. Furthermore, a superimposed image obtained by superimposing the B mode image 121 before CFAR processing and the B mode image 122 after CFAR processing is displayed, together with a microstructure extraction image.

Figure 8:
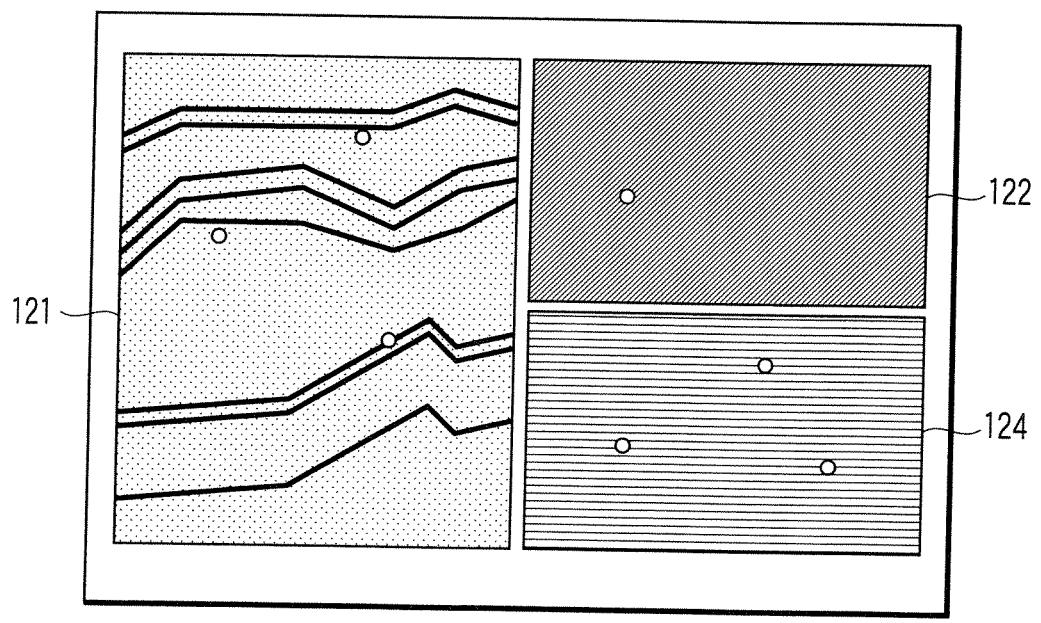
FIG. 8 is view showing still another ultrasound image display form obtained by the ultrasound diagnostic apparatus 1.

In the triplex display form, a window on the monitor 14 is divided into three parts, and different kinds of images are simultaneously displayed on the parts. According to this triplex display form, for example, as shown in FIG. 8, a microstructure extraction image 124, the B mode image 121 in which microstructures on the microstructure extraction image are acquired, and the B mode image 122 obtained by performing CFAR processing for the B mode image are simultaneously displayed.

(Operation)

Operation in image processing/display processing using the above microstructure extraction function will be described next. According to this embodiment, after a microstructure extraction image is generated, any of a B mode image before CFAR processing, a B mode image after CFAR processing, and a microstructure extraction image can be singly displayed. In addition any combination of these images can be displayed in either the dual display form or the triplex display form. However, different kinds of images can be displayed in real time depending on the sequence of image processing. Operation in image processing/display processing using this microstructure extraction function will be described for each modification classified according to such differences.

Application Example 1

In Application Example 1, a B mode image and an image having undergone CFAR processing using the B mode image are displayed in the dual display mode, and after a B mode image with a predetermined number of frames is acquired, a microstructure extraction image is generated and displayed.

Figure 9:
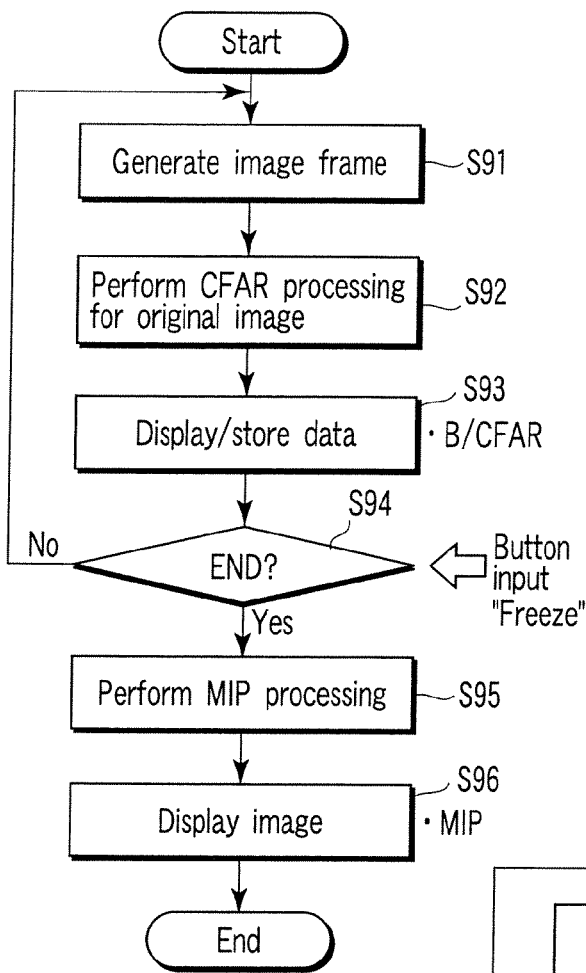
FIG. 9 is a flowchart showing the flow of processing executed in a display mode according to Application Example 1.

FIG. 9 is a flowchart showing the flow of processing executed in a display mode according to Application Example 1. Referring to FIG. 9, when the operator designates the display mode according to this modification by operating a button on an apparatus panel or the like, an image frame is generated by performing ultrasound transmission/reception according to a predetermined sequence (step S91). Note that images acquired by this ultrasound transmission/reception are so-called general B mode images.

The image processing unit 31 loads a B mode image after scan conversion into the image processing unit 31 to perform CFAR processing for it (step S92). The image having undergone CFAR processing is automatically stored in the internal storage unit 29 and sent out to the image combining unit 27. The image combining unit 27 generates a composite image comprising the images of the same frame after and before the CFAR processing, and sends out the composite image to the monitor 14. The monitor 14 simultaneously displays the B mode images before and after the CFAR processing in the dual display form (step S93).

The processing in steps S91 to S93 is repeatedly performed for acquired B mode images, and the B mode images before and after the CFAR processing are displayed as a moving image in real time in, for example, the form shown in FIG. 7 (step S94).

When the operator inputs a "FREEZE" instruction by operating the end button or the like, ultrasound transmission/reception is terminated. The image processing unit 31 calls up images having undergone CFAR processing from the internal storage unit 29, and executes MIP processing for the CFAR images from the start to the end of the operation (step S95). The microstructure extraction image obtained by the MIP processing is displayed in a predetermined form (step S96).

Note that the MIP processing in step S95 may be performed by using a method of designating the start and end frames in the MIP processing while reactivating the data recorded on the cine memory 26.

Application Example 2

In Application Example 2, a microstructure extraction image is generated after CFAR processing is executed for a B mode image with a predetermined number of frames, and the microstructure extraction image and the B mode image before the CFAR processing or the B mode image after the CFAR processing are displayed in the dual display form, or the microstructure extraction image, the B mode image before the CFAR processing, and the B mode image after the CFAR processing are displayed in the triplex display form.

Figure 10:
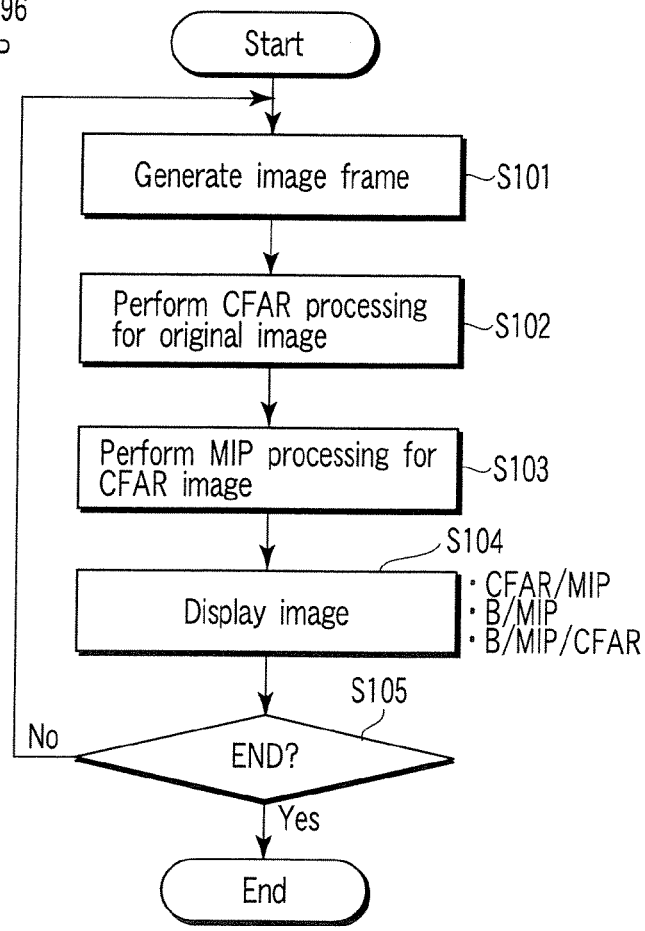
FIG. 10 is a flowchart showing the flow of processing executed in a display mode according to Application Example 2.

FIG. 10 is a flowchart showing the flow of processing executed in a display mode according to Application Example 2. Referring to FIG. 10, when the operator designates the display mode according to this modification by, for example, operating a button on the apparatus panel, an image frame is generated by performing ultrasound transmission/reception according to a predetermined sequence (step S101).

The image processing unit 31 then executes CFAR processing for a B mode image with acquired frames (step S102). An image having undergone the CFAR processing is automatically stored in the internal storage unit 29. The image processing unit 31 calls up an image or images having undergone the CFAR processing from the internal storage unit 29, and executes MIP processing (step S103). The microstructure extraction image obtained by this MIP processing is combined with a B mode image (before CFAR processing) or a B mode image after CFAR processing stored in the internal storage unit 29 as needed, and are displayed in the dual display form or the triplex display form (step S104). Note that the processing in steps S101 to S104 is repeatedly executed, as needed (step S105).

Application Example 3

In Application Example 3, a superimposed image is generated from a B mode image before CFAR processing and a B mode image after CFAR processing, and is displayed together with a microstructure extraction image.

Figure 11:
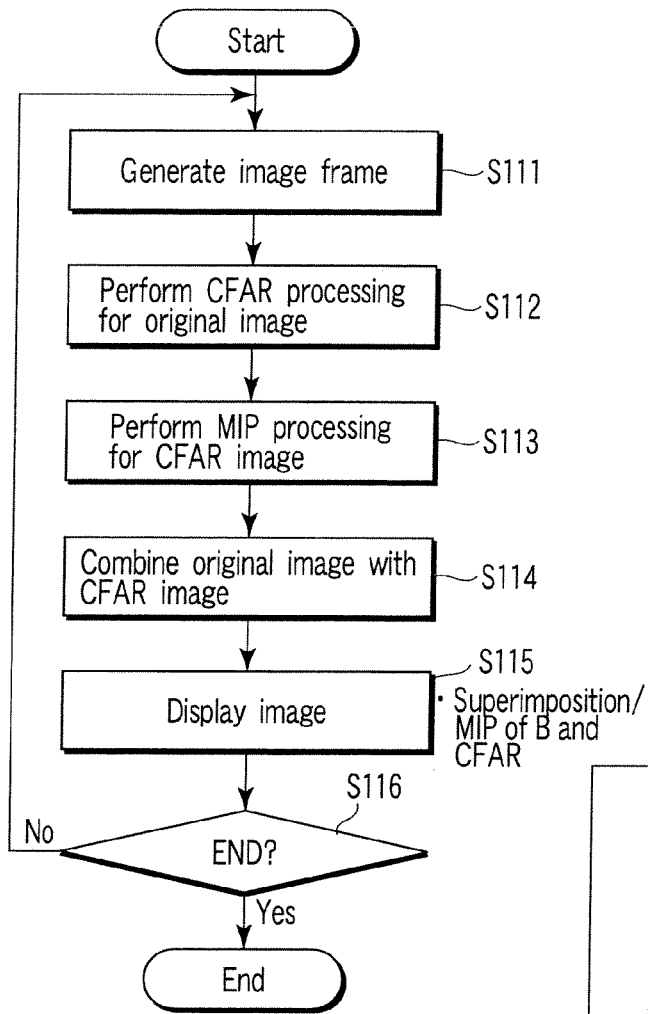
FIG. 11 is a flowchart showing the flow of processing executed in a display mode according to Application Example 3.

FIG. 11 is a flowchart showing the flow of processing executed in a display mode according to Application Example 3. Referring to FIG. 11, when the operator designates the display mode according to this modification by, for example, operating a button on the apparatus panel, an image frame is generated by performing ultrasound transmission/reception in accordance with a predetermined sequence (step S111).

The image processing unit 31 then executes CFAR processing for a B mode image with acquired frames (step S112). An image having undergone the CFAR processing is automatically stored in the internal storage unit 29. The image processing unit 31 calls up an image or images having undergone the CFAR processing from the internal storage unit 29, and executes MIP processing (step S113).

The image combining unit 27 generates a superimposed image by superimposing (combining) an image before CFAR processing and an image after CFAR processing (step S114). This image is preferably generated by superimposing (combining) a B mode image and an image after CFAR processing upon changing one or both of the color tones of the images (e.g., changing the color tone of the B mode image to blue without changing the color tone (gray) of the image after CFAR processing).

The superimposed image and the microstructure extraction image are displayed in a predetermined form (step S115), and the processing in steps S111 to S115 is repeatedly executed, as needed (step S116). Note that if a B mode image before CFAR processing or the like is read out from the internal storage unit 29 and combined with the above images, the readout image can be displayed in the triplex display form, together with the superimposed image and the microstructure extraction image.

(Effects)

According to the above arrangement, the following effects can be obtained.

According to this ultrasound diagnostic apparatus, for example, in diagnosis of the breasts, liver, pancreas, and the like, removing a speckle pattern from a B mode image and performing MIP processing make it possible to generate a microstructure extraction image. A doctor or the like can quickly find a microstructure, which is difficult to discriminate from a speckle pattern by visual observation and appears in only a specific slice image, by observing this microstructure extraction image. When a living body is three-dimensionally scanned as well, this technique can reduce the oversight of microstructures, improve the diagnosis accuracy, and shorten the diagnosis time.

In addition, this ultrasound diagnostic apparatus can read out desired images of a B mode image before speckle pattern removal, a B mode image after speckle pattern removal, and a microstructure extraction image stored in the storage unit, and can display the readout images in a predetermined form such as the dual display form or the triplex display form. In each display form in which different kinds of images are simultaneously displayed, the cursor is located in each image so as to correspond to the same position. Therefore, an observer such as a doctor can display a microstructure extraction image in a desired display form at a desired timing in accordance with a purpose, and can quickly and easily specify and observe a microstructure by using a plurality of kinds of images.

In addition, this ultrasound diagnostic apparatus can automatically specify a frame of a B mode image in which a microstructure on a microstructure extraction image is acquired. Therefore, an observer such as a doctor can specify a microstructure by a microstructure extraction image, and observe a more precise tissue image by using a B mode image in which the microstructure is acquired, thereby contributing an improvement in the quality of medical activity.

In the present embodiment, the signal processing for removing speckle patterns can be performed by using a frame image. Furthermore, the MIP processing is performed by using at least two frame image. To perform the microstructure extraction function according to the present embodiment, the 3-D image processing system is not necessary. Consequently, an ultrasound diagnostic apparatus which allows to perform the microstructure extraction function and is relatively inexpensive can be realized.

Second Embodiment

An ultrasound diagnostic apparatus 1 according to the second embodiment will be described next. The ultrasound diagnostic apparatus 1 according to the first embodiment generates a microstructure extraction image by performing MIP processing by using a B mode image corresponding to a plurality of frames after CFAR processing. In contrast to this, the ultrasound diagnostic apparatus 1 according to the second embodiment generates a microstructure extraction image by executing MIP processing by using a B mode image corresponding to a plurality of frames (before CFAR processing) and then performing CFAR processing.

Figure 12:
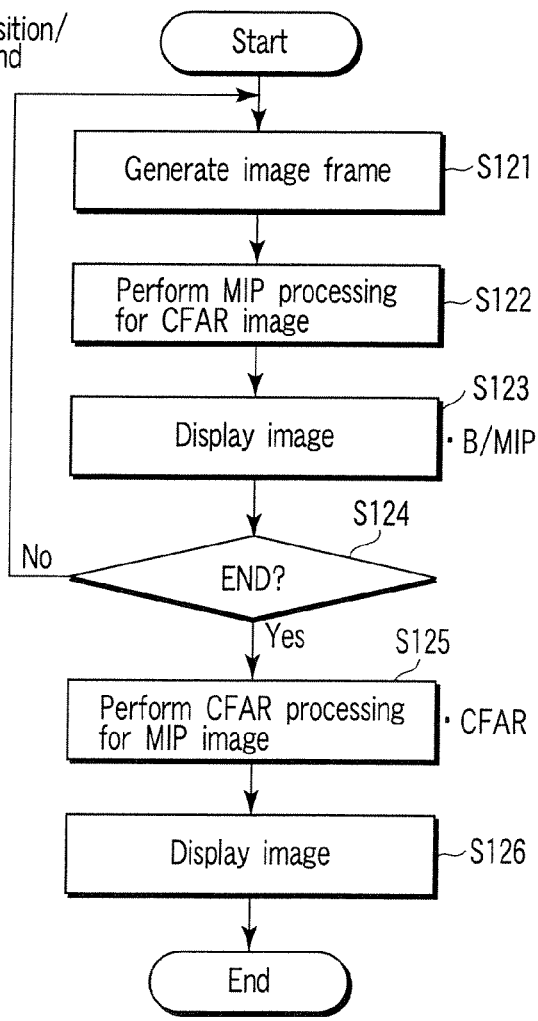
FIG. 12 is a flowchart showing the flow of processing for the generation of a microstructure extraction image by the ultrasound diagnostic apparatus according to the second embodiment.

FIG. 12 is a flowchart showing the flow of microstructure extraction image generation processing by the ultrasound diagnostic apparatus according to this embodiment. Referring to FIG. 12, when the operator designates a predetermined display mode by, for example, operating a button on the apparatus panel, an image frame is generated by performing ultrasound transmission/reception in accordance with a predetermined sequence (step S121).

An image processing unit 31 then executes MIP processing by performing peak trace processing using B mode images sequentially input from a scan converter 25 (step S122). The image having undergone the MIP processing is displayed in the dual display form on a monitor 14, together with a B mode image (step S123). Note that the processing in steps S121 to S123 is performed until ultrasound scanning in a predetermined range is executed (step S124).

The image processing unit 31 then generates a microstructure extraction image by performing CFAR processing for the MIP image obtained in step S122 (step S125). An image combining unit 27 generates the microstructure extraction image singly or generates composite image data to be displayed together with another image as needed, and sends out the generated data to the monitor 14. The monitor 14 displays the microstructure extraction image (or the composite image including it) (step S126).

With the above arrangement as well, a microstructure extraction image can be generated and displayed. According to the study made by the present inventor, when the technique according to this embodiment is compared with the technique according to the first embodiment, it is expected that a better effect can be obtained in many cases by the technique according to the first embodiment (i.e., the technique of performing MIP processing after CFAR processing).

Third Embodiment

The third embodiment of the present invention will be described next. This embodiment will exemplify another arrangement of an ultrasound diagnostic apparatus 1 which realizes the same functions and effects as those of the first and second embodiments.

FIG. 13 is a block diagram showing the arrangement of the ultrasound diagnostic apparatus 1 according to the third embodiment. FIG. 13 differs from FIG. 1 in the flow of data between a cine memory 26, internal storage unit 29, and image processing unit 31. In the ultrasound diagnostic apparatus according to this embodiment, image data recorded on the cine memory 26 is sent to the image processing unit 31, and CFAR processing and MIP processing are performed for the data. This image data is raw data before scan conversion, and hence the image processing unit 31 needs to be configured to be capable of executing scan conversion processing as well.

With the above arrangement, the same functions and effects as those of the first and second embodiments can also be realized.

Fourth Embodiment

The fourth embodiment of the present invention will be described next. This embodiment will exemplify another arrangement of an ultrasound diagnostic apparatus 1 which realizes the same functions and effects as those of the first and second embodiments.

Figure 14:
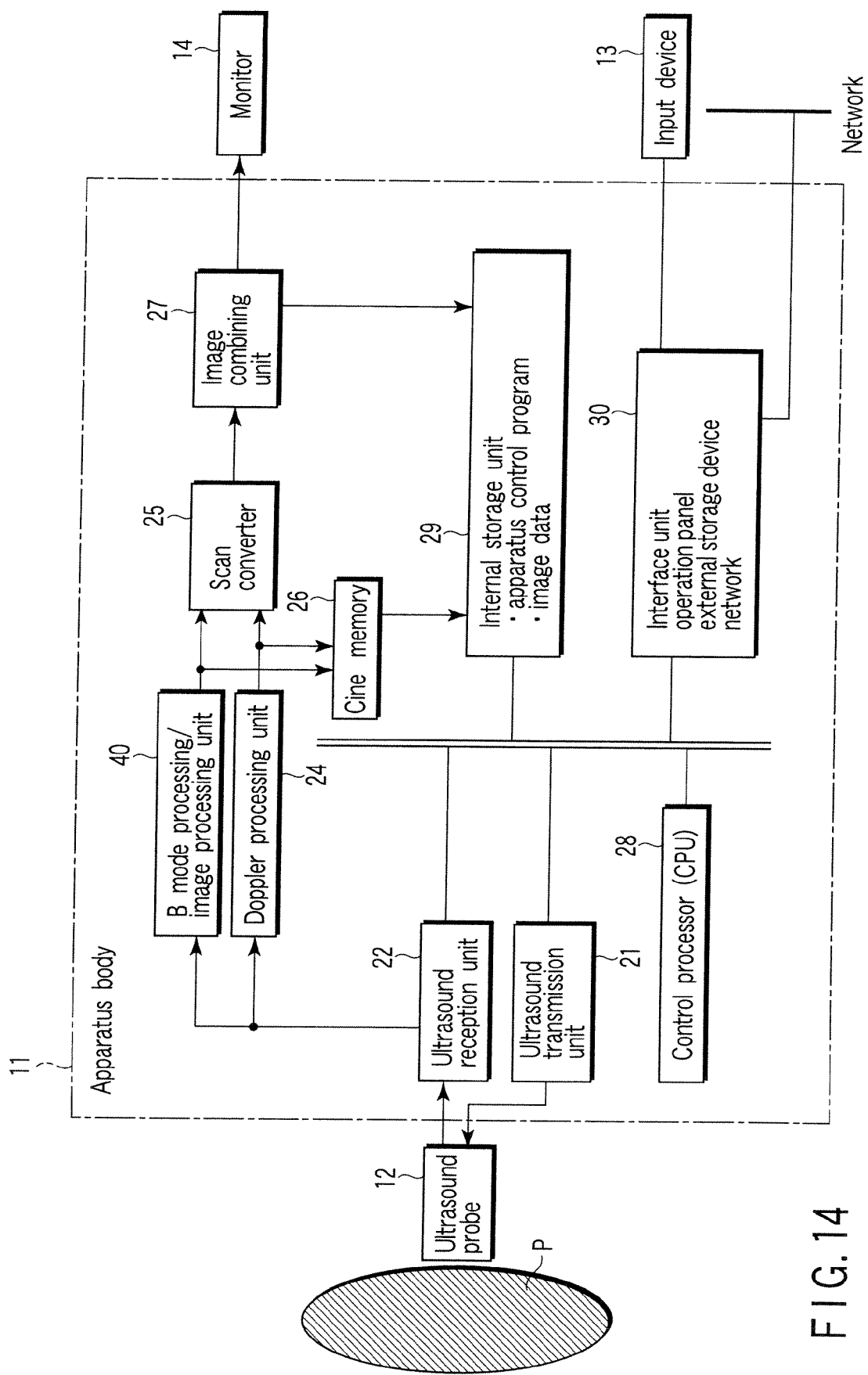
FIG. 14 is a block diagram showing the arrangement of an ultrasound diagnostic apparatus 1 according to the fourth embodiment.

FIG. 14 is a block diagram showing the arrangement of the ultrasound diagnostic apparatus 1 according to the fourth embodiment. FIG. 14 differs from FIG. 1 in that this apparatus comprises a B mode processing/image processing unit 40 instead of the B mode processing unit 23, and does not comprise the image processing unit 31.

The B mode processing/image processing unit 40 has the function of the image processing unit 31 in addition to the function of the B mode processing unit 23. That is, the B mode processing unit 23 generates a B mode image and also generates another image having undergone CFAR processing (or spatial high-pass filter processing) (an image after CFAR processing). The B mode processing unit 23 then transfers the image to a scan converter 25. After scan conversion, the above two types of images are combined to be displayed side by side by the image combining unit, and are displayed on the monitor.

With the above arrangement, the same functions and effects as those of the first and second embodiments can be realized.

Fifth Embodiment

The fifth embodiment of the present invention will be described next. In this embodiment, the form of a filter to be used to reduce speckle pattern components is arbitrarily changed depending on a diagnosis target, speckle patterns produced thereby, and various purposes, e.g., shortening the computation time. Note that the arrangement according to this embodiment can also be applied to any of the ultrasound diagnostic apparatuses according to the first to fourth embodiments.

FIGS. 15A, 15B, and 15C each show an example of a kernel used for CFAR processing executed by the ultrasound diagnostic apparatus according to this embodiment. A black pixel in the center of each kernel is a target pixel, and the above CFAR processing is performed by using an average brightness value obtained from intermediate (between white and black) pixels around the target pixel. In this case, the size of each kernel is 21×21=441 pixels. However, in to shorten the computation time, each kernel can be used upon thinning out proper pixels as shown in FIGS. 15A to 15C.

When an operator operates a kernel setting button on an input device 13, a CFAR processing control program stored in an internal storage unit 29 is read out and mapped on the memory area of a control processor 28. At the same time, for example, the window shown in FIG. 15A is displayed. For example, when the operator clicks an unselected (white) pixel in this window, the pixel is selected (turned into an intermediate color (between white and black) pixel). In contrast, when the operator clicks a selected pixel, the pixel is unselected. In this manner, the operator can arbitrarily change the positions and number of pixels to be used for computation.

The operator can also set arbitrary kernel patterns like those shown in FIGS. 15B and 15C. That is, the kernel pattern shown in FIG. 15B which has a relatively random arrangement can be set to reduce interference due to a regular arrangement as compared with the relatively isotropic pattern shown in FIG. 15A. The kernel pattern shown in FIG. 15C is an example of an arrangement for acquiring more pixels in the horizontal direction. For example, this pattern is effective in canceling a muscle tissue pattern in an image in which such muscle tissue is noticeable in the horizontal direction. Note that a plurality of kernel patterns may be prepared in advance, and the operator may select a desired pattern from them through a selection window.

The above description has exemplified the case wherein the operator sets a desired kernel pattern by himself/herself. However, the present invention is not limited to this. For example, this apparatus may be configured to inhibit changes on the user side and allow only the manufacturer to set/change a kernel pattern at the time of shipment or maintenance.

According to the above arrangement, CFAR processing can be quickly and easily implemented in accordance with a diagnosis target, speckle patterns generated thereby, and various purposes or situations, e.g., shortening the computation time. As a consequence, a more suitable microstructure extraction image can be generated and provided.

Sixth Embodiment

The sixth embodiment of the present invention will be described next. This embodiment has a function (scanning range determination function) of automatically determining whether the entire region of a diagnosis target is completely ultrasound-scanned and presenting the determination result to an operator. Note that this scanning range determination function can be provided for any of the ultrasound diagnostic apparatuses according to the first to fifth embodiments.

FIG. 16 is a block diagram showing an arrangement obtained by making the ultrasound diagnostic apparatus 1 according to the first embodiment have this scanning range determination function. FIG. 16 differs from FIG. 1 in that this apparatus further comprises a position sensor 31, magnetism generator 32, and position detection unit 33.

The magnetism generator 32 generates a magnetic field in a space containing a diagnosis target and an ultrasound probe 12, and sends out data concerning the generated magnetic field to the position detection unit 33.

The position sensor 31 detects a change in magnetic field by moving in the magnetic field.

The position detection unit 33 detects the three-dimensional moving amount of the ultrasound probe 12 on the basis of the data received from the magnetism generator 32 and the change in magnetic field detected by the position sensor.

MIP processing executed in the first to fifth embodiments is executed by using a plurality of images obtained by three-dimensionally scanning a space. Obviously, in this case, it is preferable that the entire region of an organ as a diagnosis target be entirely scanned. A control processor 28 generates information by which it can be determined whether the entire region of the diagnosis target is scanned (i.e., the scanned region of the diagnosis target) by using the body mark shown in FIGS. 17A and 17B on the basis of the three-dimensional moving amount of the ultrasound probe 12 which is detected by the position detection unit 33.

Figure 17A:
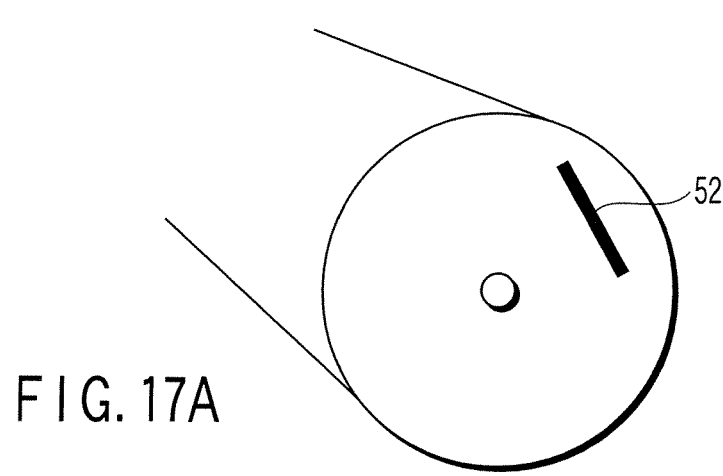
FIGS. 17A and 17B are views for explaining a body mark used in ultrasound diagnosis.
Figure 17B:
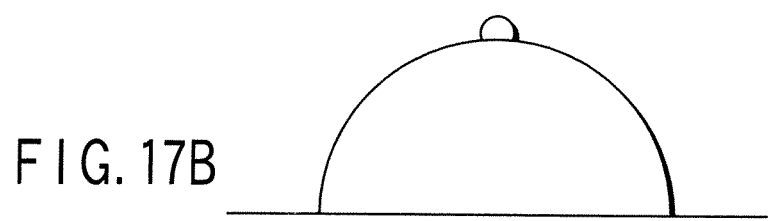

Note that a body mark is a schematic view showing an ultrasound scanning region and direction, and can be displayed, like character information, on a monitor 14, together with an ultrasound image by an image combining unit 27. A probe mark 52 in FIG. 17A is also used in general. This mark is added to a body mark by the operator to indicate a direction in which the probe is brought into contact with the breast.

Figure 18A:
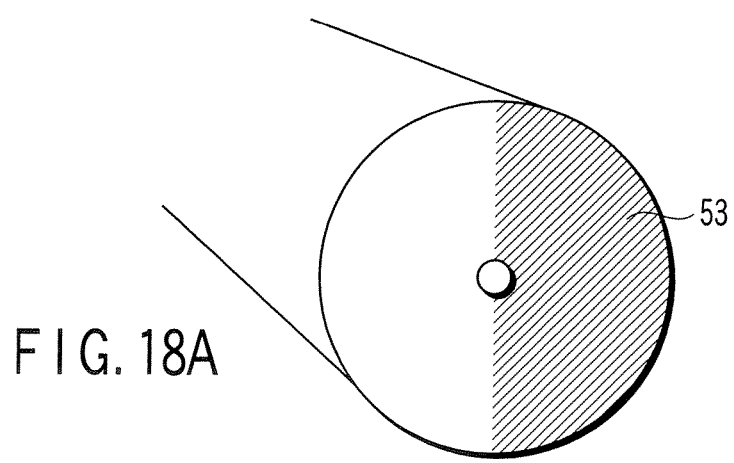
FIGS. 18A and 18B are views showing an example of how scanned regions are displayed in different colors by using a body mark.
Figure 18B:
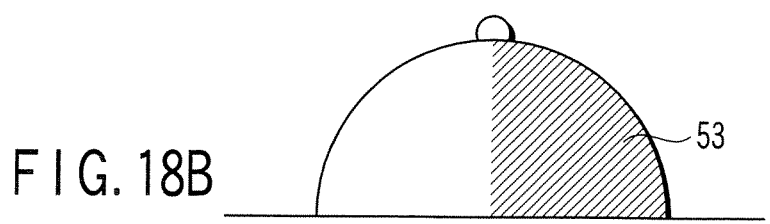

According to this scanning range determination function, first of all, a body mark generation program stored in an internal storage unit 29 is activated in response to a predetermined instruction from an input device 13 and is mapped on the memory of the control processor 28. The control processor 28 generates a new body mark on which a scanned region is displayed in a different color, like that shown in FIGS. 18A and 18B, on the basis of the body mark generation program and the three-dimensional moving amount of the ultrasound probe 12 from the position detection unit 33. The generated body mark is combined with an ultrasound image by the image combining unit 27 and displayed on the monitor 14. By observing the body mark, an operator such as a doctor can determine whether the entire region of the diagnosis target is scanned, and comprehend a non-scanned region, and the like.

In some cases, ultrasound scanning is executed a plurality of number of times with respect to the same diagnosis target as needed. In such a case, the body mark shown in FIGS. 18A and 18B may be generated and displayed every time ultrasound scanning is performed for an MIP processing target. Alternatively, different colors may be assigned to the same body mark depending on the numbers of times of ultrasound scanning.

Figure 19A:
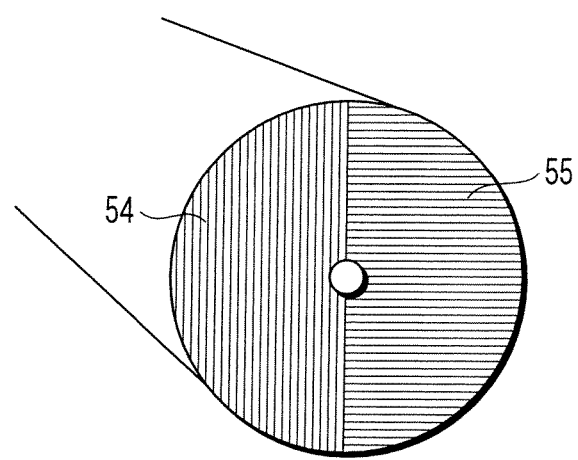
FIGS. 19A and 19B are views showing another example of how scanned regions are displayed in different colors by using a body mark.
Figure 19B:
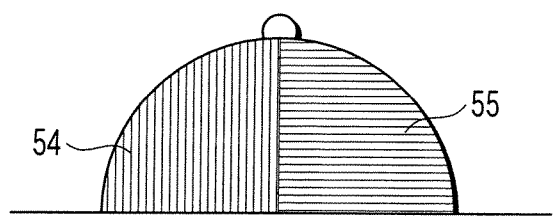

FIGS. 19A and 19B are views showing another example of how scanned regions are displayed in different colors by using a body mark. Referring to FIGS. 19A and 19B, one MIP image is generated by one three-dimensional scanning operation, and the scanned region is indicated by oblique lines 54. When the second MIP image is generated by another three-dimensional scanning operation again, the scanned region is indicated by different oblique lines 55. Such a display form allows the operator to check an omission of a scanned region. In addition, if an abnormal finding is observed in an MIP image, this display form allows the operator to easily discriminate a corresponding local region. Furthermore, a scanned region can be stored as a body mark on an image, leading to an improvement in examination efficiency.

According to the above arrangement, this apparatus can automatically determine whether the entire region of a diagnosis target is completely ultrasound-scanned without any omission, and present the result to the operator. Therefore, the operator can easily recognize a diagnosis target region which has already been ultrasound-scanned and a diagnosis target region which has not been ultrasound-scanned. This can prevent the operator from forgetting to perform examination and the like. In addition, the operator can comprehend in which region of a diagnosis target a microstructure specified by a microstructure extraction image or the like is actually located. This can contribute to an improvement in the quality of medical activities.

Note that the present invention is not limited to the above embodiments, and can be implemented by modifying constituent elements in the execution stage within the spirit and scope of the present invention. As a concrete modification, for example, the respective functions of the respective embodiments can be implemented by installing programs for executing the corresponding processes in a computer such as a workstation and mapping them on the memory. In this case, the programs which can cause the computer to execute the corresponding techniques can be distributed by being stored in recording media such as magnetic disks (floppy (registered trademark) disks, hard disks, and the like), optical disks (CD-ROMs, DVDs, and the like), and semiconductor memories.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasound diagnostic apparatus which acquires an ultrasound image by ultrasound-scanning a breast, comprising:
an ultrasound probe and a transmission/reception circuit configured to transmit ultrasound waves to the breast, receive the ultrasound waves from the breast and generate echo signals corresponding to a plurality of frames of substantially a same region at different times on the basis of the received ultrasound waves in a same scan sequence;
an image processor configured to (1) generate first images corresponding to the plurality of frames by performing signal processing, the signal processing reducing a speckle pattern component included in each of the echo signals corresponding to the plurality of frames, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves, (2) extract a component due to micro calcification occurring in breast tissue as a symptom of breast cancer, and (3) generate second images by performing maximum value projection processing or maximum value holding processing among values of the echo signals at spatially corresponding positions of the first images, which correspond to the different times; and
a display which displays the generated second images.

2. An apparatus according to claim 1, wherein the signal processing of reducing the speckle pattern component is processing using a spatial high-pass filter.

3. An apparatus according to claim 1, wherein the display simultaneously displays at least two images selected from a group consisting of a third image generated on the basis of the echo signals of the plurality of frames, the first images, and the second images.

4. An apparatus according to claim 1, wherein the display simultaneously displays a superimposed image obtained by superimposing the first images on a third image generated on the basis of the echo signals of the plurality of frames and the second images.

5. An apparatus according to claim 1, wherein the image processor is further configured to change a form of a filter when the filter is used in the signal processing of reducing a speckle pattern component.

6. An apparatus according to claim 1, further comprising a sensor configured to detect a change in a magnetic field, the change being used to determine a moving range of the ultrasound probe,
wherein the image processor is further configured to calculate an ultrasound-scanned region of the breast on the basis of the determined moving range of the ultrasound probe, wherein
the display displays the calculated ultrasound-scanned region in a predetermined form.

7. An apparatus according to claim 1, wherein the display displays an ultrasound-scanned region calculated by using a body mark.

8. The apparatus according to claim 1, wherein the image processor is further configured to perform Maximum Intensity Projection (MIP) processing for images on the same coordinates in a plurality of frames on the images.

9. The apparatus according to claim 8, wherein the image processor is further configured to perform the MIP processing using a plurality of frames that are time continuous.

10. An ultrasound diagnostic apparatus which acquires an ultrasound image by ultrasound-scanning a breast, comprising:
an ultrasound probe and a transmission/reception circuit configured to transmit ultrasound waves to the breast, receive the ultrasound waves from the breast and generates echo signals corresponding to a plurality of frames of substantially a same region at different times on the basis of the received ultrasound waves in a same scan sequence;
an image processor configured to (1) generate first images corresponding to the plurality of frames by performing maximum value projection processing or maximum value holding processing among values of the echo signals at spatially corresponding positions of said plurality of frames, which correspond to the different times, (2) generates second images by performing signal processing, the signal processing reducing a speckle pattern component included in the second images, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves, and (3) extract a component due to micro calcification occurring in breast tissue as a symptom of breast cancer; and
a display which displays the generated second images.

11. An apparatus according to claim 10, wherein the signal processing of reducing the speckle pattern component is processing using a spatial high-pass filter.

12. An apparatus according to claim 10, wherein the display simultaneously displays at least two images selected from a group consisting of a third image generated on the basis of the echo signals of the plurality of frames, the first images, and the second images.

13. An apparatus according to claim 10, wherein the display simultaneously displays a superimposed image obtained by superimposing the first images on a third image generated on the basis of the echo signals of the plurality of frames and the second images.

14. An apparatus according to claim 10, wherein the image processor is further configured to change a form of a filter when the filter is used in the signal processing of reducing a speckle pattern component.

15. An apparatus according to claim 10, further comprising a sensor configured to detect a change in a magnetic field, the change being used to determine a moving range of the ultrasound probe,
wherein the display displays the calculated ultrasound-scanned region in a predetermined form.

16. An apparatus according to claim 10, wherein the display unit displays the ultrasound-scanned region calculated by using a body mark.

17. A non-transitory computer readable medium including computer executable instructions, wherein the instructions, when executed by a processor, cause the processor to perform an ultrasound diagnostic method comprising:

generating, by performing signal processing, first images corresponding to a plurality of frames of substantially a same region at different times of a breast, the plurality of frames acquired in a same scan sequence, the signal processing reducing a speckle pattern component included in echo signals corresponding to the plurality of frames, and extracting a component due to micro calcification occurring in breast tissue as a symptom of breast cancer, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves;

generating second images by performing maximum value projection processing or maximum value holding processing among values of the echo signals at spatially corresponding positions of the first images, which correspond to the different times; and displaying the generated second images.

18. A non-transitory computer readable medium including computer executable instructions, wherein the instructions, when executed by a processor, cause the processor to perform an ultrasound diagnostic method comprising:

generating first images corresponding to a plurality of frames, acquired in a same scan sequence, of substantially a same region at different times of a breast by performing maximum value projection processing or maximum value holding processing among values of the echo signals at spatially corresponding positions of said plurality of frames, which correspond to the different times;

generating second images by performing signal processing, the signal processing reducing a speckle pattern component included in the second images, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves;

extracting a component due to micro calcification occurring in breast tissue as a symptom of breast cancer; and displaying the generated second images.

19. A control method of an ultrasound diagnostic apparatus which acquires an ultrasound image by ultrasound-scanning a breast, comprising:

transmitting ultrasound waves to the breast;
receiving the ultrasound waves from the breast;
generating echo signals corresponding to a plurality of frames of substantially a same region at different times on the basis of the received ultrasound waves in a same scan sequence;

generating first images corresponding to the plurality of frames by performing signal processing, the signal processing reducing a speckle pattern component included in each of the echo signals corresponding to the plurality of frames, and extracting a component due to micro calcification occurring in breast tissue as a symptom of breast cancer, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves;

generating second images by performing maximum value projection processing or maximum value holding processing among values of the echo signals at spatially corresponding positions of the first images, which correspond to the different times; and displaying the generated second images.

20. A control method of an ultrasound diagnostic apparatus which acquires an ultrasound image by ultrasound-scanning a breast, comprising:

transmitting ultrasound waves to the breast;
receiving the ultrasound waves from the breast;
generating echo signals corresponding to a plurality of frames of substantially a same region at different times on the basis of the received ultrasound waves in a same scan sequence;

generating first images corresponding to the plurality of frames by performing maximum value projection processing or maximum value holding processing among values of the echo signals at spatially corresponding positions of said plurality of frames, which correspond to the different times;

generating second images by performing signal processing, the signal processing reducing a speckle pattern component included in the second images, wherein the signal processing of reducing the speckle pattern components is CFAR (Contrast False Alarm Rate) processing, and the signal processing of reducing the speckle pattern components uses a kernel pattern having an arrangement to acquire more echo signals in a plurality of positions in a horizontal direction than echo signals in a plurality of positions in a vertical direction, wherein the vertical direction corresponds to a direction of transmitting the ultrasound waves;

extracting a component due to micro calcification occurring in breast tissue as a symptom of breast cancer; and displaying the generated second images.

* * * * *